(12) United States Patent
Nelson et al.

(10) Patent No.: US 8,394,948 B2
(45) Date of Patent: Mar. 12, 2013

(54) REAGENTS UTILIZING A SERINOL SCAFFOLD FOR LABELING SYNTHETIC OLIGONUCLEOTIDES

(75) Inventors: Paul S. Nelson, Morgan Hill, CA (US); Hugh Mackie, Round Hill, VA (US); Andrew Murphy, Brookeville, MD (US)

(73) Assignees: Glen Research Corporation, Sterling, VA (US); Nelson Biotechnologies, Inc., Morgan Hill, CA (US)

( * ) Notice: Subject to any disclaimer, the term of this patent is extended or adjusted under 35 U.S.C. 154(b) by 0 days.

(21) Appl. No.: 12/891,888

(22) Filed: Sep. 28, 2010

(65) Prior Publication Data

US 2011/0077389 A1 Mar. 31, 2011

Related U.S. Application Data

(60) Provisional application No. 61/247,020, filed on Sep. 30, 2009.

(51) Int. Cl.
*C07H 21/00* (2006.01)
*C07F 9/22* (2006.01)

(52) U.S. Cl. ............... 536/25.32; 536/25.34; 562/10

(58) Field of Classification Search .................. None
See application file for complete search history.

(56) References Cited

U.S. PATENT DOCUMENTS

| | | | | |
|---|---|---|---|---|
| 4,500,707 A * | 2/1985 | Caruthers et al. | ........... | 536/25.34 |
| 4,668,777 A * | 5/1987 | Caruthers et al. | ............ | 536/26.5 |
| 5,132,418 A * | 7/1992 | Caruthers et al. | ............ | 536/25.3 |
| 5,141,813 A | 8/1992 | Nelson | | |
| 5,401,837 A | 3/1995 | Nelson | | |
| 5,451,463 A | 9/1995 | Nelson et al. | | |
| 5,519,134 A * | 5/1996 | Acevedo et al. | .............. | 544/243 |
| 5,567,811 A | 10/1996 | Misiura et al. | | |
| 5,585,481 A | 12/1996 | Arnold, Jr. et al. | | |
| 5,637,684 A * | 6/1997 | Cook et al. | .................. | 536/23.1 |
| 5,717,083 A * | 2/1998 | Cook et al. | .................. | 536/23.1 |
| 5,736,626 A * | 4/1998 | Mullah et al. | ................ | 536/25.3 |
| 5,942,610 A | 8/1999 | Nelson et al. | | |
| 6,184,389 B1 * | 2/2001 | Hebert | ............................ | 506/15 |
| 6,448,373 B1 * | 9/2002 | Cook et al. | ................... | 530/300 |
| 6,828,427 B1 * | 12/2004 | Hebert | ......................... | 536/23.1 |
| 6,875,850 B2 * | 4/2005 | Heindl et al. | ................ | 536/22.1 |
| 7,144,995 B2 * | 12/2006 | Wise et al. | ..................... | 536/4.1 |
| 7,615,618 B2 * | 11/2009 | Manoharan et al. | ......... | 536/22.1 |
| 7,626,014 B2 * | 12/2009 | Manoharan et al. | ......... | 536/24.5 |
| 7,705,136 B2 * | 4/2010 | Golova et al. | ................ | 536/23.1 |
| 7,723,512 B2 * | 5/2010 | Manoharan et al. | ......... | 536/27.1 |
| 8,013,136 B2 * | 9/2011 | Manoharan et al. | ......... | 536/23.1 |
| 2005/0208199 A1 * | 9/2005 | Golova et al. | ................ | 427/2.11 |

OTHER PUBLICATIONS

Vu et al. (I), "Synthesis and Properties of Cholesteryl-Modified Triple-Helix Forming Oligonucleotides Containing a Triglycinyl linker," Bioconjugate Chemistry, 5(6), 666-668 (Nov. 1994).*
Vu et al. (II), "Use of Phthaloyl Protecting Group for the Automated Synthesis of 3'-[(Hydroxypropyl)amino] and 3'-[(Hydroxypropyl)triglycyl] Oligonucleotide Conjugates," Bioconjugate Chemistry, 6(5), 599-607 (Sep. 1995).*
Nelson et al., "Oligonucleotide labeling methods 3. Direct labeling of oligonucleotides employing a novel, non-nucleosidic, 2-aminobutyl-1,3-propanediol backbone" Nucleic Acids Research; 1992, vol. 20, No. 23, pp. 6253-6259.
Nelson et al.,"A new versatile reagent for incorporating multiple primary aliphatic amines into synthetic oligonucleotides" Nucleic Acids Research; 1989, vol. 17, No. 18, pp. 7179-7186.
Nelson et al., "Bifunctional oligonucleotide probes synthesized using a novel CPG support are able to detect single base pair mutations" Nucleic Acids Research; 1989, vol. 17, No. 18, pp. 7187-7194.
Konrad et al., "Biotinyl and phosphotyrosinyl phosphoramidite derivatives useful in the incorporation of multiple reporter groups on synthetic oligonucleotides" Nucleic Acids Research, 1990, vol. 18, No. 15, pp. 4345-4354.
Putnam et al.,"Efficient new ribozyme mimics: direct mapping of molecular design principles from small molecules to macromolecular, biomimetic catalysts" Nucleic Acids Research, 2001, vol. 29, No. 10, pp. 2199-2204.
Shchepinov et al., "Steric factors influencing hybridisation of nucleic acids to oligonucleotide arrays" Nucleic Acids Research, 1997, vol. 25, No. 6, pp. 1155-1161.

* cited by examiner

*Primary Examiner* — Lawrence E Crane
(74) *Attorney, Agent, or Firm* — Banner & Witcoff, Ltd.

(57) ABSTRACT

Novel CE-phosphoramidites and CPG reagents have been synthesized from a serinol backbone. These reagents are useful to introduce functional groups or directly label oligonucleotides. The versatile serinol scaffold allows for labeling at any position (5' or 3' termini, or any internal position) during automated DNA synthesis. Multiple labels or functional groups can be achieved by repetitive coupling cycles. Optimal spacer arms and protected label moieties have been specially designed. Further, the natural 3-carbon atom internucleotide phosphate distance is retained when inserted internally.

24 Claims, No Drawings

REAGENTS UTILIZING A SERINOL SCAFFOLD FOR LABELING SYNTHETIC OLIGONUCLEOTIDES

This application claim priority to U.S. Ser. No. 61/247,020 filed Sep. 30, 2009, which disclosure is incorporated by reference in its entirety.

BACKGROUND OF THE INVENTION

Current methods to introduce chemical modifications into oligonucleotides have limitations. Many non-nucleosidic phosphoramidite reagents are limited to single modifications at the 5' terminus, thus terminating chain elongation at the point of introduction. Those designed for multiple incorporations such as 1,2-diol backbone phosphoramidite reagents also suffer some drawbacks. The internucleotide distance, when incorporated internally, results in a constricted internucleotide phosphate distance one carbon atom shorter than the natural DNA structure. Further, the 1,2-diol backbone can participate in a dephosphorylation reaction due to a highly favorable 5-membered cyclic phosphate intermediate, resulting in cleavage of the label. Other reagents suffer from poor design in protecting label moieties. For example, some biotin phosphoramidite reagents do not protect its urea moiety. Hence, phosphoramidites can react at this active position of biotin in unwanted side reactions.

The 1,3 diol reagents of Nelson et at have proven to be superior, overcoming the above disadvantages, albeit, improved protection of label moieties have not been addressed. The subject of this invention builds upon the advantages of the 1,3 diol reagents by utilizing a serinol backbone. This backbone is versatile, readily available, and allows for convenient preparation of reagents. The purpose of this invention is to overcome the disadvantages encountered in the prior art by providing improved reagents to directly modify or label oligonucleotides via automated DNA synthesis.

BRIEF SUMMARY OF INVENTION

The subject invention concerns reagents prepared from a serinol scaffold that are used to introduce functional groups or directly label oligonucleotides via automated DNA synthesis, having the following structure:

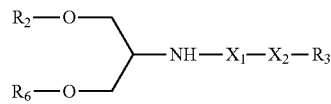

wherein:
$R_1$=DMT, MMT, or any other hydroxyl protecting group stable to oligonucleotide synthesis conditions.
$R_2$=phosphoramidite or phosphate group consisting of and salts thereof; wherein $R_3$ and $R_4$ are independently selected from the group consisting of $C_{1-10}$ branched alkyl, $C_{1-12}$ alkyl, and cyclic hydrocarbons; and $R_5$ is any phosphate-protecting group. In a preferred embodiment $R_3=R_4=$—$CH(CH_3)_2$ and $R_5=$—O—$(CH_2)_2$—CN.

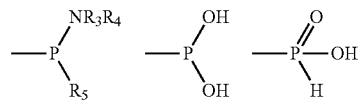

$R_2$ can also be controlled pore glass (CPG); alkylamine CPG; wherein alkyl is 1-50 carbon atoms and isomeric forms thereof; chemically modified CPG; or suitable polymer; such polymers are know to those skilled in the art and include, for example polystyrene and divinylbenzene.

$X_1$=spacer group that separates $X_2$ from the serinol amino functional group (—NH—). A preferred embodiment of $X_1$ is —CO—CH2-CH2-.

$X_2$=a functional group such as an amine, (—NH2), or sulfhydryl (—SH), or hydroxyl (—OH) which can be utilized for attaching a label or other desired molecule.

$R_6$=any reporter molecule including but not limited to biotin, carboxyfluorescein, propargyl, haptens, stable in oligonucleotide synthesis conditions; or any protecting group for the functional group $X_2$.

Preferred phosphoramidite embodiments are compounds 5, 6, 7, and 20. Preferred CPG embodiments are compounds 8, 9, 10, 12, and 21. See Schemes 1-8.

The reagents of the subject invention are useful in oligonucleotide synthesis to chemically modify a synthetic oligonucleotide at any position, with any chemical functional group or label. Reagents where $R_2$ is a phosphoramidite are useful for modifications at the 5' terminus or at any internal locations. Reagents where $R_2$ is a solid support such as CPG, are useful for modifications at the 3' terminus.

The reagents of the subject invention can be used to directly modify any oligonucleotide with single or multiple functional groups (—NH2, —SH, OH, —COOH). such as primary amines. Preferred embodiments 5 & 8 are examples of structures that incorporate primary amines. The incorporated functional groups can be subsequently labeled with reporter molecules such as biotin, fluorescein, and other haptens. Molecules such as proteins, enzymes, and antibodies can also be attached to the functionally modified oligonucleotides.

The reagents of the subject invention can be used to directly label any oligonucleotide with single or multiple labels. Preferred embodiments 6, 7, 9, 10, 12, 20, and 21 represent reagents in this category.

Synthetic oligonucleotide modified with the reagents of subject invention can be used in any application where the modified oligonucleotide (probe) hybridizes to complementary sequences of a target polynucleotide. Further, primers made from reagents of subject invention can be used in the polymerase chain reaction (PCR) to amplify the target gene segment and then employing the invention for detecting the presence of specific polynucleotide in samples containing the same sequence. Such samples can include biological samples, e.g., clinical samples such a serum and blood. The subject invention can also be used for diagnosis of infectious diseases and pathogens, detection of oncogenes, diagnosis of genetic disorders, and the detection of point mutations or single base substitutions. The subject invention also has utility in the areas of anti-sense molecular biology, electron microscopy, X-ray crystallograhy, and site-specific cleavage of DNA. Another important application of the subject invention is DNA sequencing using procedures well known to those skilled in the art. In general, the subject invention can be readily used by those skilled in the art in all emerging technologies that utilize modified oligonucleotides.

The key feature of the invention is the serinol backbone. The unique serinol backbone gives the invention the following features:

1. Reagents synthesized from the serinol backbone can be utilized on any commercial olignucleotide/DNA synthesizer, and perform the same as standard nucleoside phosphoramidite and CPG reagents.
2. Serinol is a readily available and economical starting material for synthesis of all reagents of subject invention.
3. Serinol possesses a versatile molecular structure that allows for easy preparation of reagents. In particular, the 2-position amino group allows for extending a spacer group ($X_1$) of any shape or size. This is critical for spacing the label at an exact distance, or for incorporating chemical properties such hydrophobicity or hydrophillicity into the oligonucleotide. In a preferred embodiment $X_1$ is —CO—CH2-CH2-.
4. Reagents of subject invention synthesized from the serinol backbone allows for labeling and modification of synthetic oligonucleotides at any position (3', 5', or internally).
5. Phosphoramidite reagents (preferred embodiments 5, 6, 7, and 20) of subject invention synthesized from the serinol backbone ($R_2$=phospharamidite) allows for multiple labeling and modification of synthetic oligonucleotides. That is, multiple labels and units can be incorporated by repetitive coupling cycles. The subject invention provides a method for a combination of different labels to the same oligonucleotide.
6. When inserted in oligonucleotides, reagents of subject invention synthesized from the serinol backbone conserve the natural 3-carbon atom internucleotide distance between phosphate groups. This mimics and functions as the natural distance and is relevant in regards to annealing and hybridization properties.
7. CPG reagents (preferred embodiments 8, 9, 10, 12, and 21) of subject invention synthesized from the serinol backbone allows for direct modification and labeling at the 3' terminus maintaining the natural 3-carbon atom internucleotide distance. This prevents cleavage of the chemical modification by a known 5-membered cyclic ring mechanism.

DETAILED DISCLOSURE OF THE EMBODIMENTS OF THE INVENTION

The reagents of the subject invention are useful in oligonucleotide synthesis to chemically modify a synthetic oligonucleotide at any position with any chemical functional group. These reagents, which couple exactly like normal CE-phosphoramidites and CPGs, are designed for use with any automated DNA synthesizer.

EXAMPLE 1

N-Fmoc-β-Ala-Serinol (1)

Fmoc-β-alanine (84.5 g, 271 mmol) and N-hydroxysuccinimide (31.2 g, 271 mmol) are dissolved in dichloromethane (850 mL) and DMF (43 mL) with magnetic stirring. N,N-dicyclohexylcarbodiimide (56.0 g, 271 mmol) dissolved in dichloromethane (100 mL) is added in one portion. After stirring 1.5 hours at room temperature, the reaction mixture was filtered, and transferred to a mixture of serinol (24.7 g, 271 mmol) in pyridine (380 mL) and allowed to react 16 hours overnight. The mixture is evaporated to a semi-solid residue, and co-evaporated 3×400 mL toluene to remove the remaining pyridine. The solid residue is refluxed in dichloromethane (3.0 L) and stored at −20° C. for 2 hours. The product was collect by filtration in a sintered glass funnel, and washed 2×1000 mL dichloromethane, and 1×1000 mL diethyl ether. Drying overnight under high vacuum yielded 92.8 g (89%) of 1.

EXAMPLE 2

N-Fmoc-β-Ala-O-DMT-Serinol (2)

N-Fmoc-β-Ala-Serinol (1, 93 g, 242 mmol) is co-evaporated 2×400 mL anh. pyridine, and then dissolved in 300 mL of the same solvent with magnetic stirring. The mixture is cooled in a ice bath, and DMT-Cl (86.1 g, 254 mmol) in 465 mL pyridine is added dropwise over a period of 1.5 hours. The ice bath is removed and the mixture is allowed to react for another hour at room temperature. Methanol (100 mL) is added and stirred for 15 min. to quench the remaining DMT-Cl. After evaporation in vacuo, the residue co-evaporated 3×400 mL with toluene. Silica gel column purification using ethyl acetate/methanol/triethylamine (95:5:0.25) as mobile phase yielded 90.6 g (55%) grams of isolated product 2.

EXAMPLE 3

N-t-Butylbenzoyl-biotinyl-β-Ala-O-DMT-Serinol (3)

Biotin-NHS ester (7.8 g, 22.9 mmol) is suspended in 105 mL of a mixture of DMF/pyridine (1:1). 4-t-butylbenzoyl chloride (9.0 g, 45.9 mmol) is added dropwise to the reaction mixture and allowed to react overnight at room temperature. Methanol (24 mL) is added and stirring is continued for 15 min. The mixture is directly partitioned between 500 mL ethyl acetate and 200 mL water. The organic phase is washed 1×200 mL 5% bicarbonate, 1×200 brine, and dried over anh. sodium sulfate. The t-butylbenzoyl biotin-NHS ester solution is used directly in the next step.

N-Fmoc-β-Ala-O-DMT-Serinol (2, 15.0 g, 21.8 mmol) is dissolve in 150 mL isopropyl alcohol. Sodium borohydride (15 g) is added. The mixture is heated to 70° C. for 1 hour with stirring. The reaction mixture is cooled, carefully quenched with 123 mL of cold 10% sodium hydroxide solution, and partitioned with 400 mL ethyl acetate. The organic phase is separated and washed 2×200 mL brine, and dried over anh. sodium sulfate. The solvent is removed in vacuo and the resultant -Ala-O-DMT-serinol is used directly in the next step.

Both t-butylbenzoyl biotin-NHS ester solution and β-Ala-O-DMT-serinol are combined and the pH is adjusted to 7.5-8.0 (litmus paper) with triethylamine. The mixture is allowed to react overnight at room temperature, and then partitioned with 500 mL bicarbonate. The organic phase is washed 1×500 mL brine, dried over anh. sodium sulfate, and evaporated in vacuo. Flash chromatography with silica gel using ethyl acetate/methanol (95:5) followed by ethyl acetate/methanol (90:10) yielded 14.2 g (76%) of desired product 3 after evaporation.

EXAMPLE 4

6-Carboxyfluorescein-β-Ala-O-DMT-Serinol (4)

N-Fmoc-β-Ala-O-DMT-Serinol (2, 27.5 g, 40.1 mmol) is dissolved in 275 mL isopropyl alcohol. Sodium borohydride (27.5 g) is added. The mixture is heated to 70° C. for 1 hour with stirring. The reaction mixture is cooled, carefully quenched with 267 mL of cold 10% sodium hydroxide solution, and partitioned with 500 mL ethyl acetate. The organic phase is separated and washed 2×250 mL brine, and dried over anh. sodium sulfate. The solvent is removed in vacuo and the resultant β-Ala-O-DMT-serinol is used directly in the next step.

6-Carboxyfluorescein dipivolate (21.8 g, 40.1 mmol) is dissolved in 340 mL dichloromethane with magnetic stirring. N-hydroxysuccinimide (6.0 g, 52.1 mmol) is added and the mixture is cooled in an ice bath. N,N'-dicyclohexylcarbodi-imide (8.5 g, 41.3 mmol) is added, the ice bath removed, and allowed to reach for 2 hours at room temperature. The mixture is then added directed to the β-Ala-O-DMT-serinol, and allowed to react overnight at room temperature. After filtration through a sintered glass funnel, 300 mL dichloromethane is added. The organic phase is washed 1×400 mL 5% citric acid solution in 1 M sodium chloride, 3×400 mL 1.0 M sodium chloride, dried over anh. sodium sulfate, and evaporated in vacuo to dryness. Flash chromatography with silica gel using acetone/hexanes/triethylamine (25:73:2), and incrementally increasing acetone content to 45%, yielded 18.0 g (46%) of desire product 4 after evaporation.

EXAMPLE 5

General Procedure for Preparing CE-Phosphoramidites 5, 6, 7 & 20 from Precursors 2, 3, 4 & 19 Respectively 10.0 mmol of precursor (2, 3, 4, or 19) is dissolved in 75 mL of dry dichloromethane. Tetrazole (10.0 mmol) and 2-cyanoethyl-N,N,N',N'-tetraisopropyl-phosphorodiamidite (3.0 g, 10 mmol) are added and the mixture allowed to react for 25 min. with ice cooling. The reaction mixture is partitioned between 500 mL ethyl acetate and 400 mL 10% sodium carbonate. The organic phase is washed 3×400 mL 10% sodium carbonate, 1×400 mL brine, and dried over anh. sodium sulfate. The solvent is removed in vacuo and the product purified on a 5×45 cm column of silica gel. 150 mL fractions were collected, appropriate fractions were pooled and evaporated to dryness to give products 5, 6, 7, and 20 as diastereomeric mixtures in 50-85% yields.

EXAMPLE 6

N-Propargyl-dPEG1-β-Ala-Serinol (11)

N-Fmoc-β-Ala-O-DMT-Serinol (2, 3.5 g, 5.1 mmol) is dissolved in 35 mL isopropyl alcohol. Sodium borohydride (3.55 g) is added. The mixture is heated to 70° C. for 1 hour with stirring. The reaction mixture is cooled, carefully quenched with 29 mL of cold 10% sodium hydroxide solution, and partitioned with 200 mL ethyl acetate. The organic phase is separated, washed 2×100 mL brine, and dried over anh. sodium sulfate. The solvent is removed in vacuo and the resultant -Ala-O-DMT-serinol is used directly in the next step.

The crude β-Ala-O-DMT-serinol is dissolved in 24.5 mL dichloromethane and 1.0 g propargyl-dPEG1-NHS ester (4.6 mmol) is added. The reaction mixture is stirred for 1.0 hour with ice bath cooling. The mixture is taken up in 200 mL ethyl acetate and transferred to separatory funnel. After extraction with 2×100 mL brine and drying over anh. sodium sulfate, the solvent is removed in vacuo. Flash chromatography with silica gel using ethyl acetate/methanol (97:3), and incrementally increasing methanol content to 5%, yielded 1.4 g (48%) of desire product 11 after evaporation.

EXAMPLE 7

General Procedures for Preparing LCAA CPGs 8, 9, 10, 12 & 21 from Precursors 2, 3, 4, 11, & 19 Respectively Dissolve 2.0 mmol precursor (2, 3, 4, 11, or 19) in 5 mL 1,2-dichloroethane. Add 240 mg succinic anhydride (2.4 mmol), 122 mg DMAP (1.0 mmol), and 0.56 mL triethylamine (4.0 mmol). Heat a 50° C. for 45 min. Add 75 mL ethyl acetate and transfer to separatory funnel. Wash organic layer with 3×35 mL 5% ice cold citric acid, 3×35 mL water, 1×35 mL brine, and dry over anh. sodium sulfate. Add 2 mL pyridine and evaporate in vacuo. Take up in 100 mL dichloromethane. Add 0.56 mL triethylamine (4.0 mmol), 270 mg HBT (2.0 mmol) and 25 grams 1000 angstrom LCAA CPG. Finally, add 885 mg BOP (2.0 mmol) and immediately swirl to mix. Agitate 2 hours on an orbital shaker. Collect modified CPG by filtration and copiously wash 3× with DMF, 5× with methanol, and 2× diethyl ether. Dry under high vacuum for 1 hour.

The CPG is capped with pyridine-acetic anhydride-DMAP solution, reacting from 0.25-1.0 hour. The CPG is collected by filtration and thoroughly washed 2× pyridine, 3×DMF, 4× dichloromethane, 5× methanol, and 2× diethyl ether. Drying overnight under high vacuum gives modified LCAA CPGs 8, 9, 10, 12, and 21 respectively.

EXAMPLE 8

4,7,10-trioxa-1,13-tridecanediamine-diglycolicylate (13)

Dissolve 187 mL 7,7,10-trioxa-1,13-tridecanediamine (852 mmol) in 1000 mL dichloromethane. Add 33 g (284 mmol) diglycolic anhydride and allow to react 18 hours overnight at room temperature. Evaporate in vacuo to a thick syrup. Take up in 350 mL dichloromethane and triturate with 1050 mL diethyl ether. Repeat two times. Flash chromatography with silica gel using methanol/dichloromethane/triethylamine (25:70:5), and incrementally increasing methanol content to 30%, yielded 39 g (40%) of desire product 13 after evaporation.

EXAMPLE 9

N-t-butylbenzoyl-biotin NHS Ester (14)

Dissolve 35 g Biotin NHS ester (103 mmol) in 225 mL DMF and 225 mL pyridine. Add 40.5 mL 4-t-butylbenzoyl chloride (206 mmol) and react overnight at room temperature with magnetic stirring. Add 60 mL methanol and stir for another 15 minutes. Evaporate in vacuo to a thick oil. Partition between 1500 mL ethyl acetate and 300 mL 5% sodium bicarbonate. Wash 1×700 mL brine, dry over anh. sodium sulfate, and evaporate in vacuo. Co-evaporate 2×300 mL toluene. Flash chromatography with silica gel using methanol/dichloromethane (1:99) yielded 38 g (74%) of desire product 14 (isomeric mixture) after evaporation.

EXAMPLE 10

N-t-butylbenzoyl-biotinyl-4,7,10-trioxa-1,13-tridecanediamine-diglycolicylate (15)

22.3 g of 4,7,10-trioxa-1,13-tridecanediamine-diglycolicylate (1, 66 mmol) is dissolved in 400 mL dichloromethane. Triethylamine (12.6 mL, 90 mmol) and N-t-butylbenzoyl-biotin NHS Ester (14, 30.1 g, 60 mmol) are added, and the mixture is allowed to react for 4 hours with magnetic stirring at room temperature. 375 mL dichloromethane is added and the mixture is transferred to a separatory funnel. Wash organic phase 2×350 mL 2.5% aq. citric acid, dry over anh. sodium sulfate, and evaporate in vacuo to dryness. Flash chromatography with silica gel using methanol/ethyl acetate (20:80), and incrementally increasing ethyl acetate content to 60%, gave 33.7 g (59%) of desire product 15 after evaporation.

EXAMPLE 11

N-TFA-amino-1-O-DMT-1,3-propanediol (17)

Into a 1 L round bottom flask, add 26.7 g 2-amino-1,3-propanediol (Serinol, 292 mmol) and 62.9 mL methyl trifluoroacetate (630 mmol). Carefully add 55.5 mL triethylamine (399 mmol) with magnetic stirring at room temperature. Stir for 1 hour at room temperature. Evaporate in vacuo to give N-TFA-amino-1,3-propanediol (16). Use directly in next step.

Co-evaporate 16 3×250 mL anh. pyridine, and dissolve in 615 mL pyridine with magnetic stirring and ice cooling. Using a addition funnel, add a mixture of 89.4 g dimethoxytrityl chloride (263 mmol) in 400 mL pyridine over a period of 1 hour. Allow to react 1.0 hour with continued ice cooling after the addition. Evaporate pyridine in vacuo, and partition residue between 1500 mL addition and 750 mL water. Wash organic phase 1×750 mL brine, dry over anh. sodium sulfate, and evaporate to a thick syrup. Co-evaporate 4×400 mL toluene. Flash chromatography with silica gel using ethyl acetate/hexanes/triethylamine (20:80:0.25), and incrementally increasing ethyl acetate content to 40%, yielded 79 g (55%) of desire product 17 after evaporation.

EXAMPLE 12

2-Amino-1-O-DMT-1,3-propanediol (18)

N-TFA-amino-1-O-DMT-1,3-propanediol (17, 79 g, 161 mmol) is dissolved 1070 mL isopropyl alcohol. Sodium borohydride (106 g) is added. The mixture is heated to 70° C. for 1 hour with stirring. The reaction mixture is cooled, carefully quenched with 1200 mL of cold 10% sodium hydroxide solution, and partitioned with 900 mL ethyl acetate. The organic phase is separated, washed 2×450 mL brine, and dried over anh. sodium sulfate. The solvent is removed in vacuo to yield 61 g (97%) of 18 which is used directly in the preparation of N-t-butylbenzoyl-biotinyl-4,7,10-trioxa-1,13-tridecanediamine-diglycolicyl-O-DMT-serinol 19).

EXAMPLE 13

N-t-butylbenzoyl-biotinyl-4,7,10-trioxa-1,13-tridecanediamine-diglycolicylyl-O-DMT-serinol (19)

N-t-butylbenzoyl-biotinyl-4,7,10-trioxa-1,13-tridecanediamine-diglycolicylate (15, 31.5 g, 48.5 mmol) is dissolved in 375 mL dichloromethane. BOP (43.0 g, 97 mmol), 2-Amino-1-O-DMT-1,3-propanediol (18, 19.1 g, 48.5 mmol), and diisopropylethylamine (16.9 mL, 97 mmol) are added. The mixture is allowed to react 4.5 hours with magnetic stirring at room temperature. Add 1500 mL ethyl acetate and transfer to reparatory funnel. Wash 1×500 mL water, 1×700 mL brine, dry over anh. sodium sulfate, and evaporate in vacuo. Flash chromatography with silica gel eluting with acetone then methanol/acetone (1:99) gave 19.4 g (75%) of desire product 19 (isomeric mixture) after evaporation.

EXAMPLE 14

General Procedure of Modified Oligonucleotides Using Phosphoramidite Reagents. Compounds 5, 6, 7, and 20.

Modified oligonucleotides were synthsized on an Applied Biosystems DNA synthesizer using standard manufacturer procedures for cyanoethyl phosphoramidite chemistry. The serinol phosphoramidite reagents 5, 6, 7 and 20 were used in a concentration of 0.1 M without any increased coupling times. After syntheiss of modified oligonucleotides, cleavage from CPG support and deprotection were performed by treatment with concentrated ammonium hydroxide at 55° C. for 6 hours. HPLC purification and analyses were performed employing a Grace Allshere ODS-2 column (150×4.4 mm); Solvent A=0.1 M TEAA, pH 7.0; Solvent B=50% acetonitrile, 30 minutes, 0.75 mL/min, 254 nm.

EXAMPLE 15

General Procedure of 3' Modified Oligonucleotides Using CPG Reagents. Compounds 6, 7, 9, 10, 12, 20, and 21.

3'-Modified oligonucleotides were synthsized on a Applied Biosystems DNA synthesizer using standard manufacturer procedures for cyanoethyl phosphoramidite chemistry. The serinol CPG reagents 6, 7, 9, 10, 12, 20, and 21 were packed in standard columns and installed in the DNA synthesizer in the same fashion as normal nucleoside CPG columns are used. After synthesis of modified oligonucleotides, cleavage from CPG support and deprotection were performed by treatment with concentrated ammonium hydroxide at 55° C. for 6 hours. HPLC purification and analyses were performed employing a Grace Allshere ODS-2 column (150×4.4 mm); Solvent A=0.1 M TEAA, pH 7.0; Solvent B=50% acetonitrile, 30 minutes, 0.75 mL/min, 254 nm.

Schematic 1
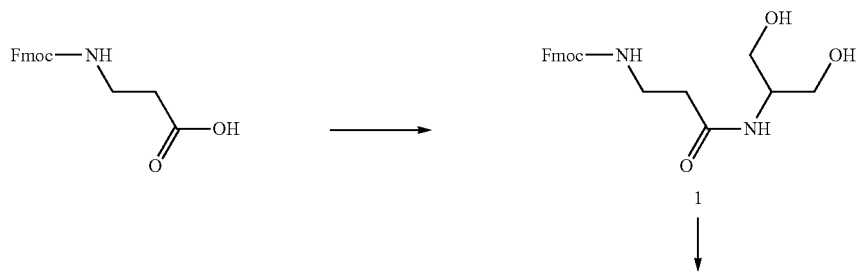
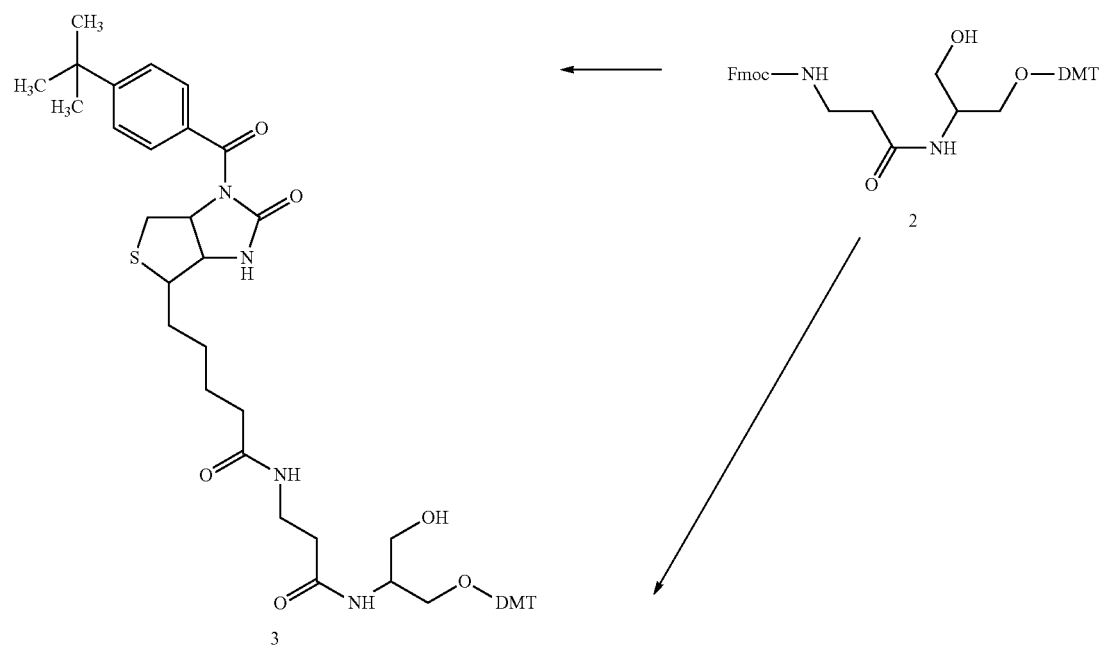
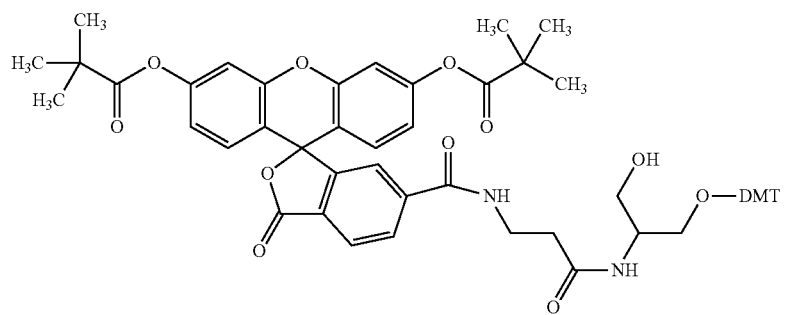

Schematic 2
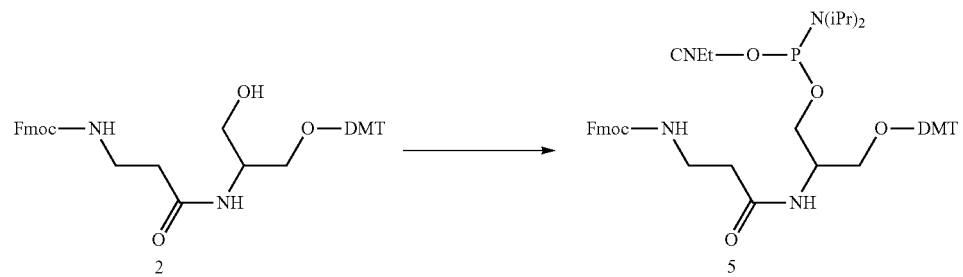
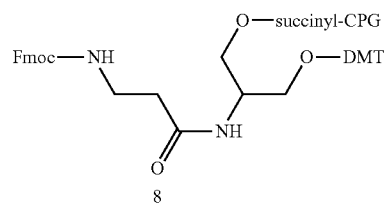
Schematic 3
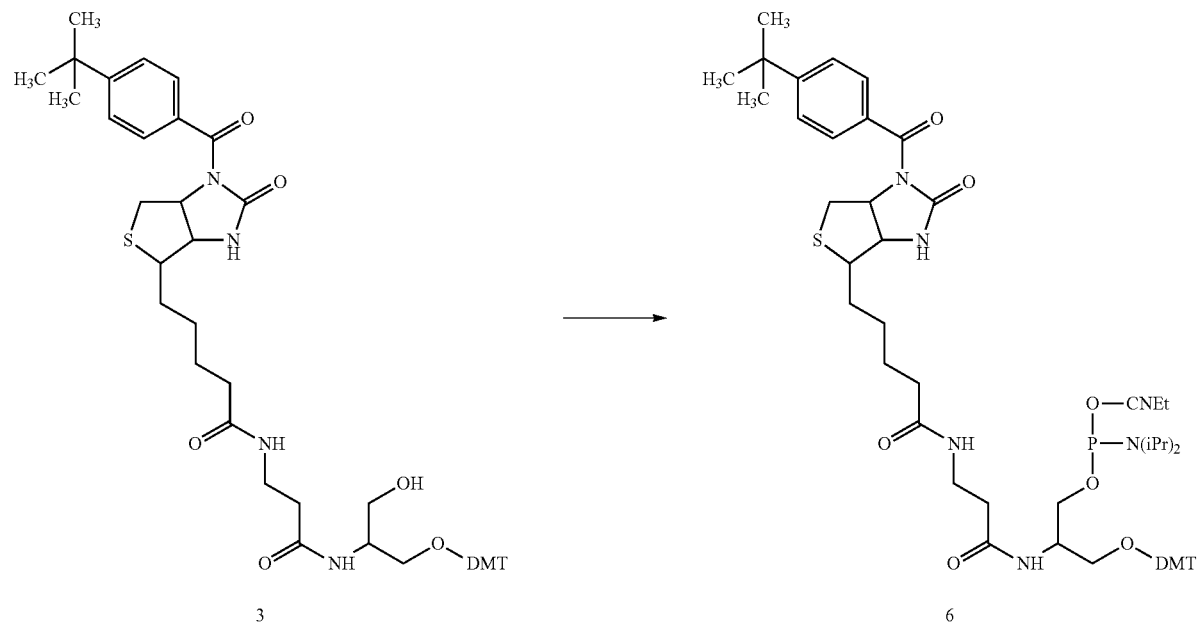

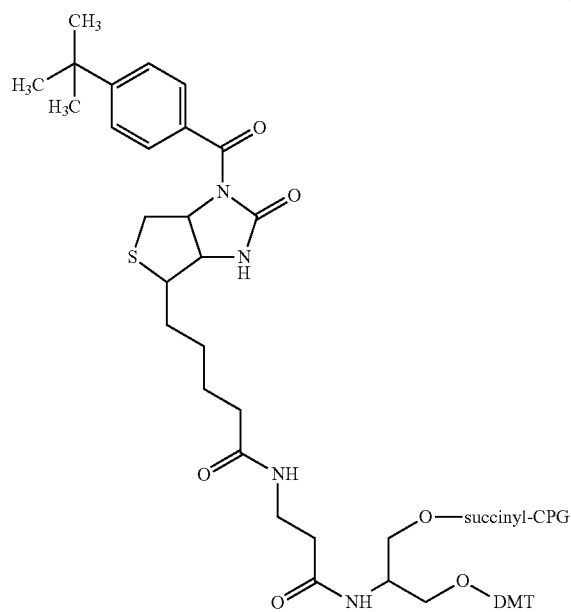
Schematic 4
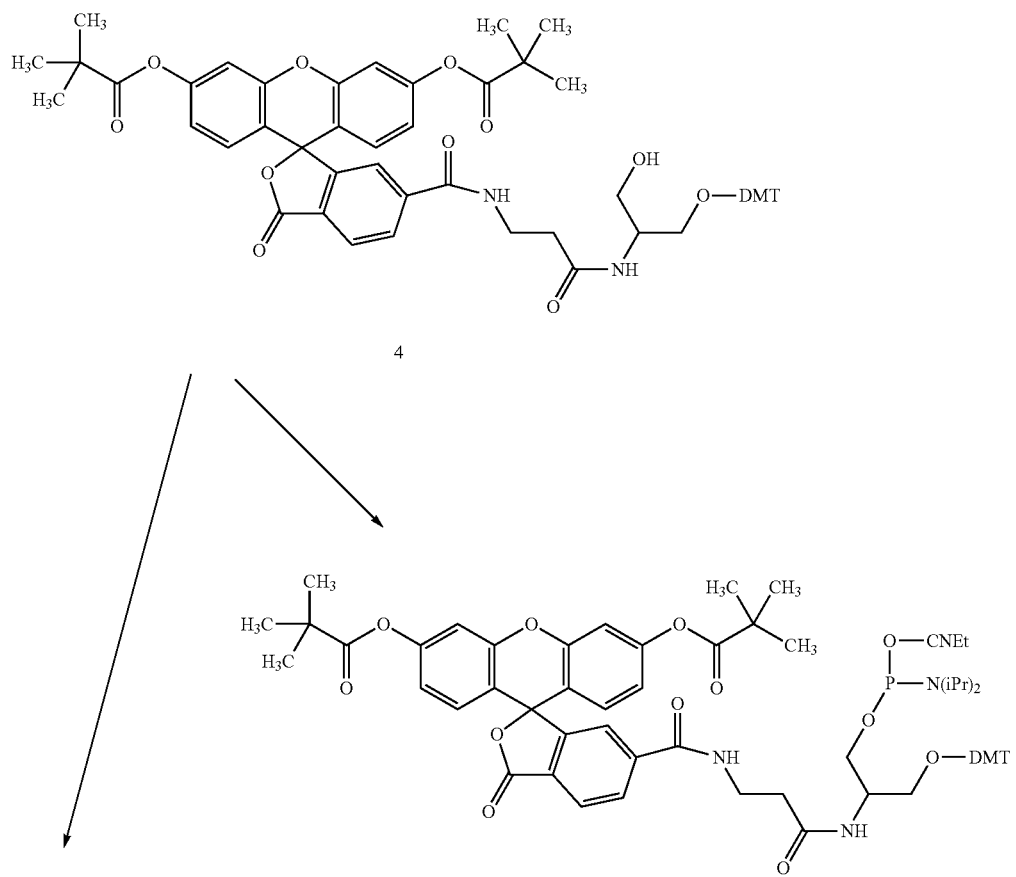

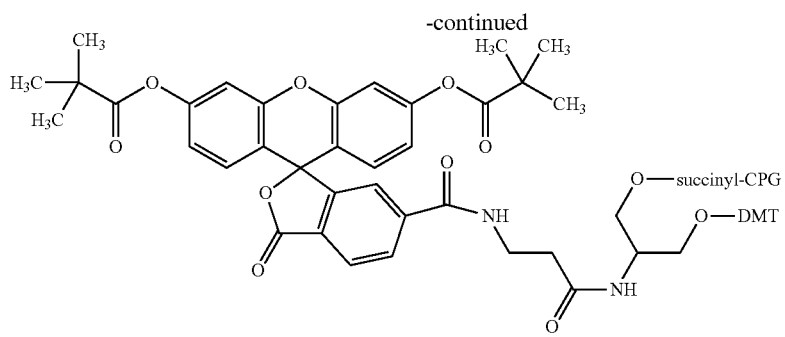
-continued
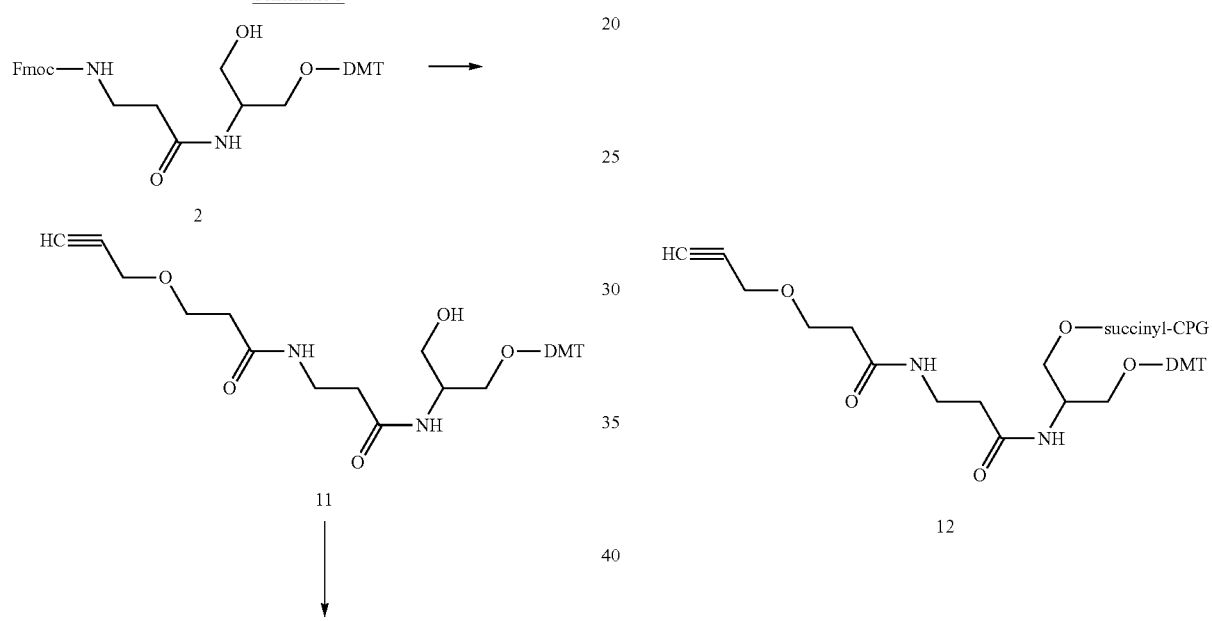
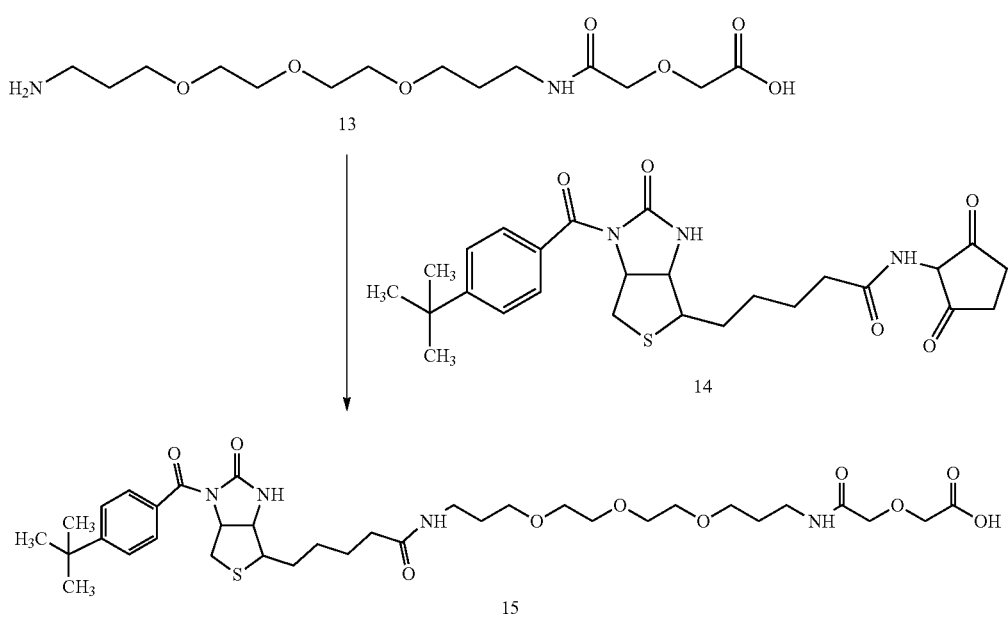

-continued
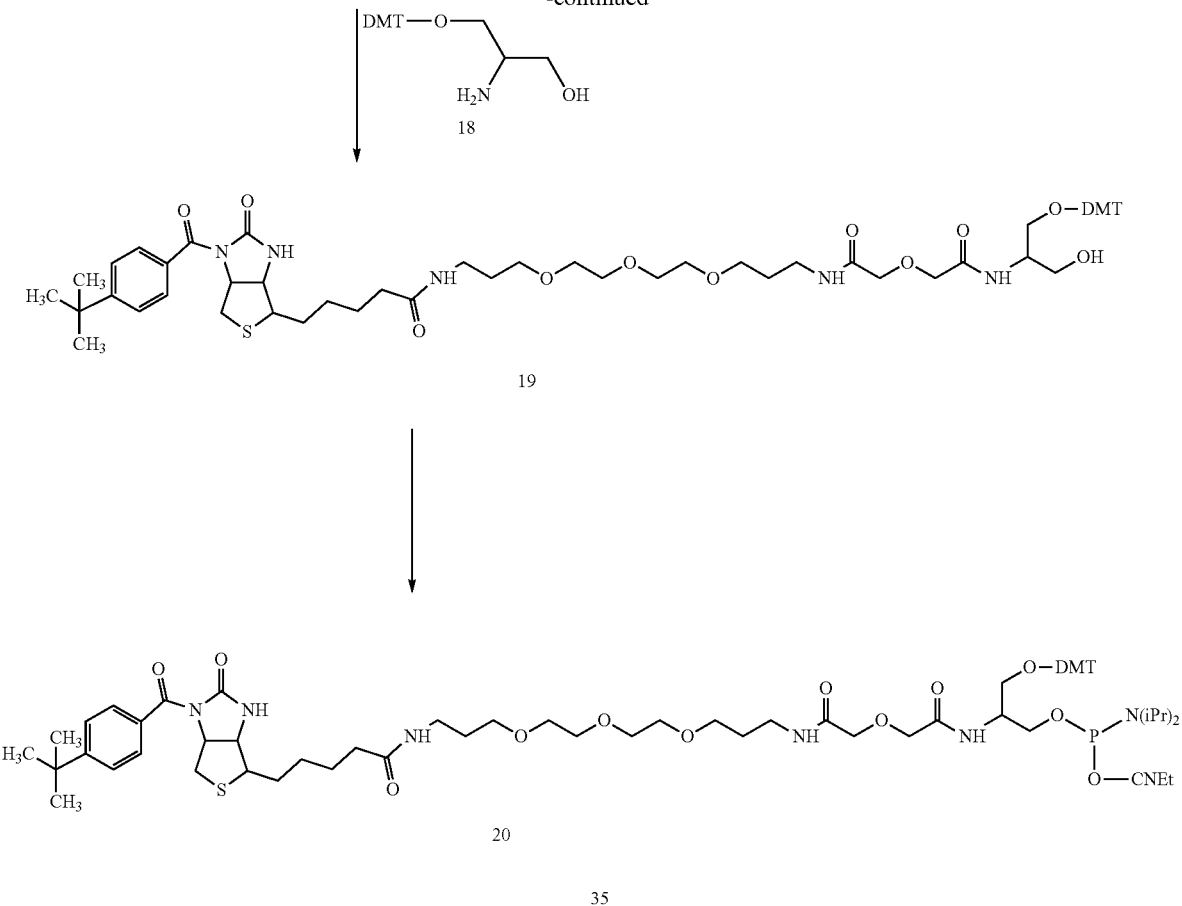
Schematic 7
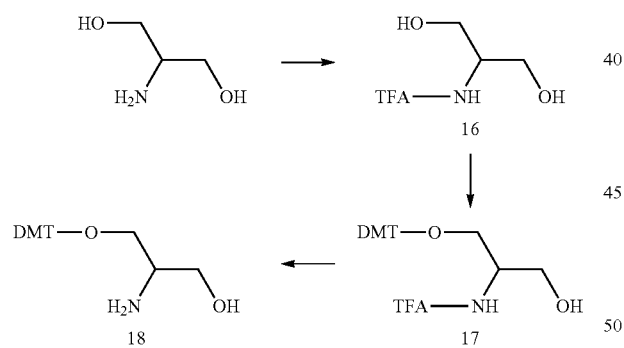
Schematic 8
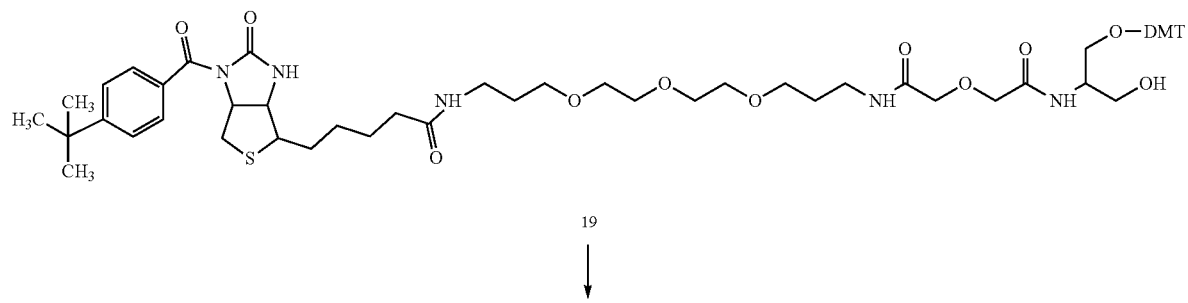

-continued

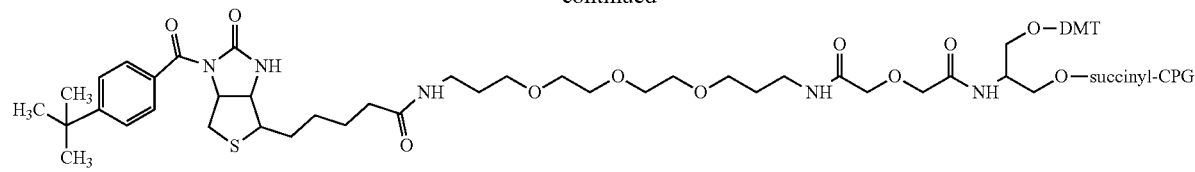

The invention claimed is:

1. A reagent having the following structure:

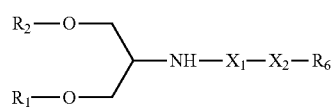

wherein:

$R_1$ = dimethoxytrityl (DMT), monomethoxytrityl (MMT), or other hydroxyl protecting group stable to oligonucleotide synthesis conditions;

$R_2$ = phosphoramidityl

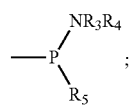

wherein $R_3$ and $R_4$ are independently selected from the group consisting of $C_{1-10}$ branched alkyl, $C_{1-12}$ alkyl, and cyclic hydrocarbyls; and $R_5$ is a phosphite-protecting group $X_1$ = —CO—$CH_2CH_2$ or —CO—$CH_2$, $X_2$ = —NH—, —S—, or —O—;

$R_6$ = a reporter substituent moiety selected from the group consisting of biotinyl, carboxyfluoresceinyl, propargyl, and a hapten-derived substituent moiety; or a suitable protecting group for $X_2$.

2. The reagent according to claim 1 wherein $R_3$=$R_4$=—CH(CH$_3$)$_2$ and $R_5$=—O—(CH$_2$)$_2$—CN.

3. The reagent according to claim 2, having the following structure (Compound 5):

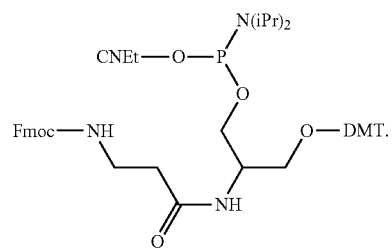

4. The reagent according to claim 2, having the following structure (Compound 6):

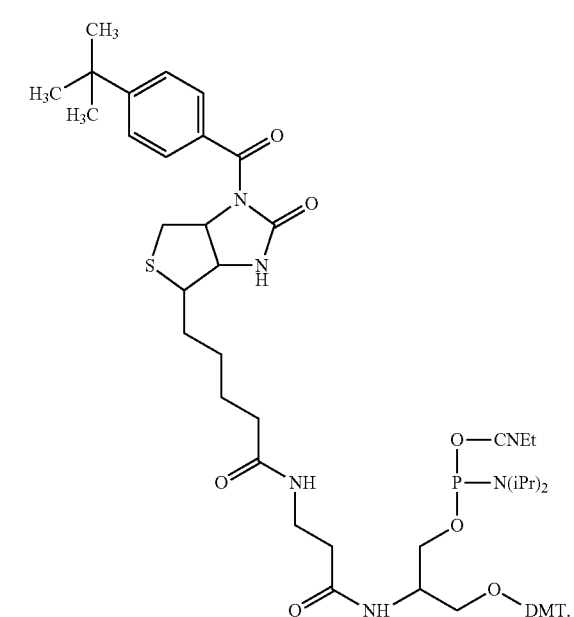

5. The reagent according to claim 2, having the following structure (Compound 7):

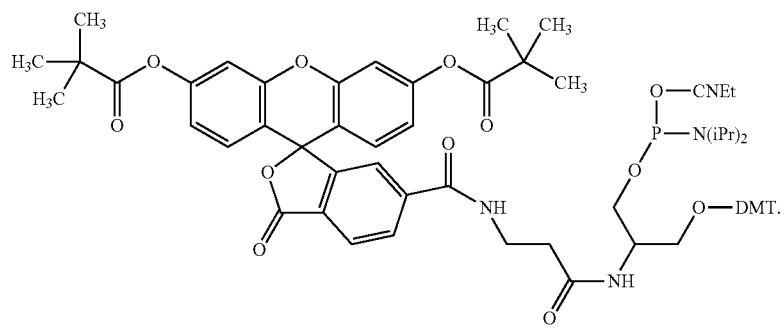

6. The reagent according to claim 2, having the following structure (Compound 20):

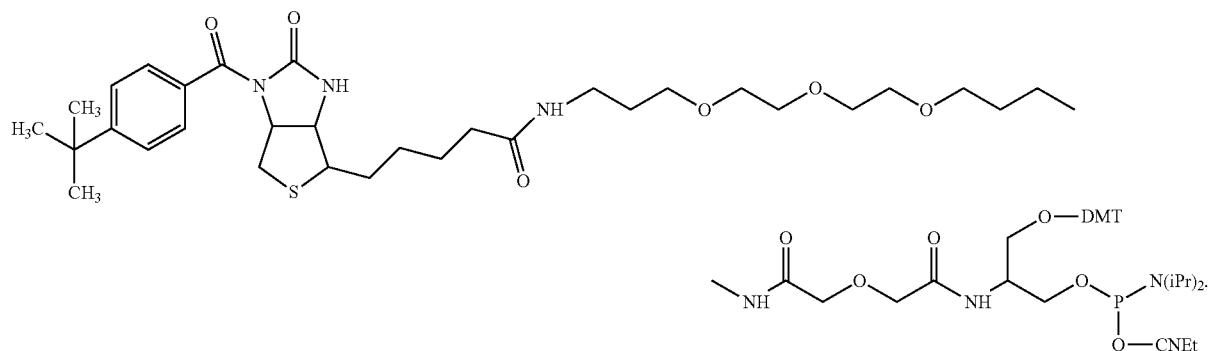

7. A process to label or modify a synthetic oligonucleotide at any nucleoside position wherein the process comprises incorporating a reagent having the structure according to claim 1 into said oligonucleotide by phosphoramidite coupling during automated oligonucleotide synthesis.

8. A process to label or modify a synthetic oligonucleotide at any nucleoside position wherein the process comprises incorporating a reagent having the structure according to claim 2 into said oligonucleotide by phosphoramidite coupling during automated oligonucleotide synthesis.

9. A process to label or modify a synthetic oligonucleotide at any nucleoside position wherein the process comprises incorporating a reagent having the structure according to claim 3 into said oligonucleotide by phosphoramidite coupling during automated oligonucleotide synthesis.

10. A process to label or modify a synthetic oligonucleotide at any nucleoside position wherein the process comprises incorporating a reagent having the structure according to claim 4 into said oligonucleotide by phosphoramidite coupling during automated oligonucleotide synthesis.

11. A process to label or modify a synthetic oligonucleotide at any nucleoside position wherein the process comprises incorporating a reagent having the structure according to claim 5 into said oligonucleotide by phosphoramidite coupling during automated oligonucleotide synthesis.

12. A process to label or modify a synthetic oligonucleotide at any nucleoside position wherein the process comprises incorporating a reagent having the structure according to claim 6 into said oligonucleotide by phosphoramidite coupling during automated oligonucleotide synthesis.

13. A reagent having the following structure:

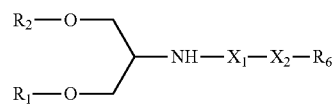

wherein:
$R_1$=dimethoxytrityl (DMT), monomethoxytrityl (MMT), or other hydroxyl protecting group stable to oligonucleotide synthesis conditions;

$R_2$ is a long chain alkyl amine controlled pore glass attached through a succinyl linkage (-succinyl-CPG);
$X_1$=—CO—CH$_2$CH$_2$ or —CO—CH$_2$;
$X_2$=—NH—, —S—, or —O—;
$R_6$=a reporter substituent moiety selected from the group consisting of biotinyl, carboxyfluoresceinyl, propargyl, and a hapten-derived substituent moiety; or a suitable protecting group for $X_2$.

14. The reagent according to claim 13, having the following structure (Compound 8):

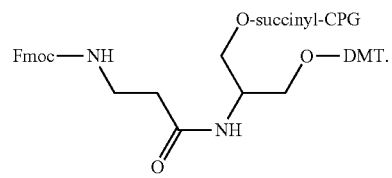

15. The reagent according to claim 13, having the following structure (Compound 9):
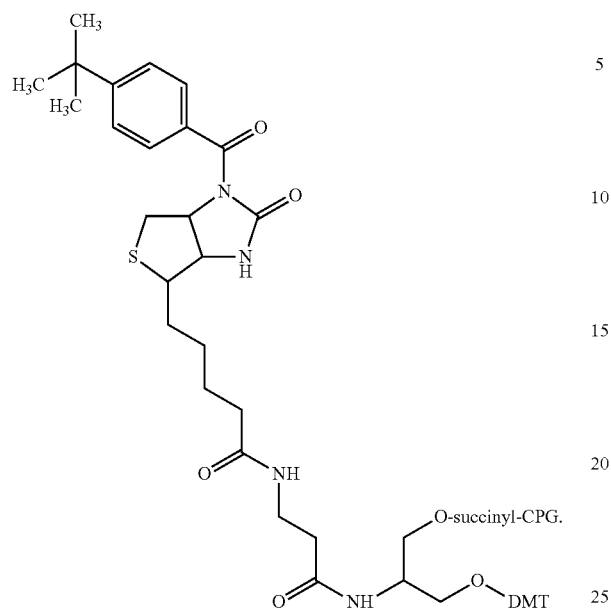
16. The reagent according to claim 13, having the following structure (Compound 10):
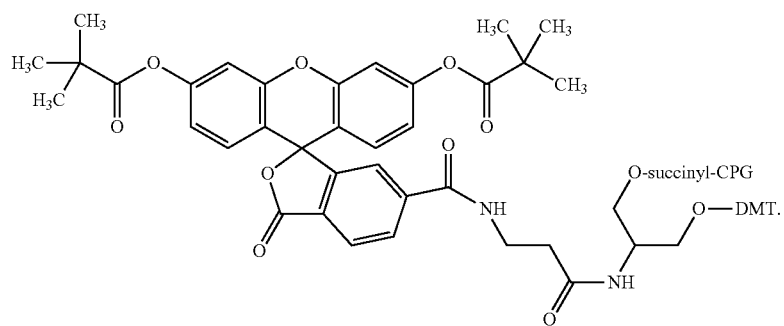
17. The reagent according to claim 13, having the following structure (Compound 12):
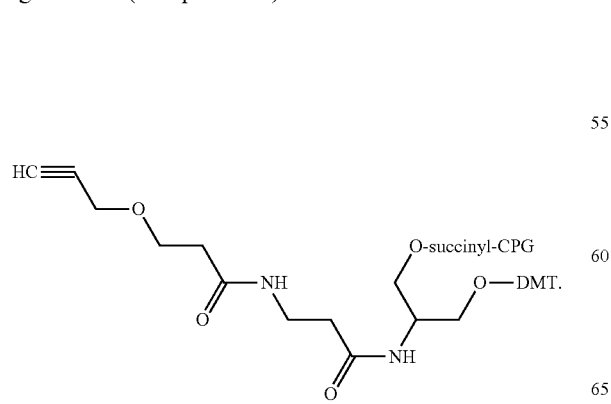

18. The reagent according to claim 13, having the following structure (Compound 21):

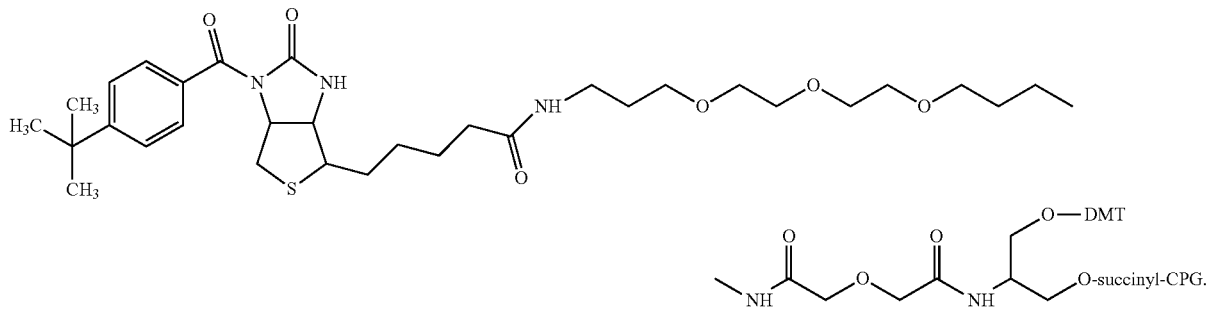

19. A process to label or modify a synthetic oligonucleotide at the 3' terminal position by substituting the reagent having the structure according to claim 14 into said oligonucleotide for a standard nucleosidic solid support in automated oligonucleotide synthesis.

20. A process to label or modify a synthetic oligonucleotide at the 3' terminal position by substituting the reagent having the structure according to claim 15 into said oligonucleotide for a standard nucleosidic solid support in automated oligonucleotide synthesis.

21. A process to label or modify a synthetic oligonucleotide at the 3' terminal position by substituting the reagent having the structure according to claim 16 into said oligonucleotide for a standard nucleosidic solid support in automated oligonucleotide synthesis.

22. A process to label or modify a synthetic oligonucleotide at the 3' terminal position by substituting the reagent having the structure according to claim 17 into said oligonucleotide for a standard nucleosidic solid support in automated oligonucleotide synthesis.

23. A process to label or modify a synthetic oligonucleotide at the 3' terminal position by substituting the reagent having the structure according to claim 18 into said oligonucleotide for a standard nucleosidic solid support in automated oligonucleotide synthesis.

24. A process to label or modify a synthetic oligonucleotide at the 3' terminal position by substituting the reagent having the structure according to claim 13 into said oligonucleotide for a standard nucleosidic solid support in automated oligonucleotide synthesis.

* * * * *